(12) United States Patent
Walzman (10) Patent No.: US 11,007,048 B2
(45) Date of Patent: May 18, 2021

(54) CAPED STENT

(71) Applicant: Daniel Ezra Walzman, Bergenfield, NJ (US)

(72) Inventor: Daniel Ezra Walzman, Bergenfield, NJ (US)

( * ) Notice: Subject to any disclaimer, the term of this patent is extended or adjusted under 35 U.S.C. 154(b) by 0 days.

(21) Appl. No.: 16/214,130

(22) Filed: Dec. 9, 2018

(65) Prior Publication Data

US 2019/0151072 A1 May 23, 2019

Related U.S. Application Data

(63) Continuation-in-part of application No. 15/732,544, filed on Nov. 22, 2017.

(60) Provisional application No. 62/497,851, filed on Dec. 5, 2016.

(51) Int. Cl.
*A61F 2/07* (2013.01)
*A61F 2/958* (2013.01)

(52) U.S. Cl.
CPC ............. *A61F 2/07* (2013.01); *A61F 2/958* (2013.01); *A61F 2002/077* (2013.01); *A61F 2210/0076* (2013.01)

(58) Field of Classification Search
CPC .............. A61F 2/07; A61F 2002/077; A61F 2210/0076; A61F 2/958
See application file for complete search history.

(56) References Cited

U.S. PATENT DOCUMENTS

| 6,379,382 | B1 | 4/2002 | Yang |
| 6,428,569 | B1 | 8/2002 | Brown |
| 6,635,082 | B1 | 10/2003 | Hossainy |
| 8,398,701 | B2 | 3/2013 | Berez |
| 2001/0049554 | A1* | 12/2001 | Ruiz ........................ A61F 2/06 623/1.44 |
| 2007/0219619 | A1 | 9/2007 | Dieck et al. |
| 2008/0281394 | A1 | 11/2008 | Jones |
| 2012/0316632 | A1 | 12/2012 | Gao |
| 2014/0025151 | A1 | 1/2014 | Gao |

FOREIGN PATENT DOCUMENTS

WO    WO2005112823 A1    12/2005

OTHER PUBLICATIONS

Chun Fang et al., Using a covered stent for large cerebral aneurysms treated with stent-assisted coiling (Interv Neuroradiol. Jun. 2015; 21(3): 317-324).

Shogo Nishi et al., Treatment of rabbit carotid aneurysms by hybrid stents (microporous thin polyurethane-covered stents): Preservation of side-branches (J Biomater Appl. 2014.

* cited by examiner

*Primary Examiner* — Christopher D. Prone (57) ABSTRACT

A caped stent providing a cover having a single attachment point and an overlappable free end providing better conformity to target vessels than existing covered stents in which the stent covering is affixed throughout such stent.

20 Claims, 5 Drawing Sheets

CAPED STENT

CROSS-REFERENCE(S)

This continuation-in-part application claims the benefit of the priority to utility patent application Ser. No. 15/732,544 filed Nov. 22, 2017 and provisional Ser. No. 62/497,851 filed Dec. 5, 2016, the contents of which are hereby incorporated by reference.

FIELD OF THE INVENTION

The present disclosure relates to medical devices used to treat aneurysms and fistulas within unhealthy blood vessels, and more particularly, relates to endovascular devices.

BACKGROUND OF THE INVENTION

Prior Art

The prior art teaches the use of a number of devices to treat aneurysms. A common blood vessel difficulty is the persistent blood flow in the aneurysm sac extrinsic to the endograft. In fact, this is the most common complication after endovascular aneurysm repair (EVAR). Such endoleaks are ameliorated by a number of means. For example, Walzman's utility application Ser. Nos. 15/732,147 and 15/732,365 teach the use of hydrogel to prevent endoleaks.

The prior art also teaches endovascular coiling as a minimally invasive technique performed to prevent blood from flowing into some saccular aneurysms. This treatment results in the coil inducing embolization (clotting) of the aneurysm, which prevents blood from flowing into the aneurysm, which in turn, prevents rupture and subsequent subarachnoid hemorrhage. Endovascular coiling however may result in procedural complications include thromboembolism, cerebral embolization, aneurysm perforation, parent artery occlusion, coil migration, arterial dissection, and others. The prior art also teaches stent-assisted coiling. The stent-assisted coiling also has some of the same short comings related to stent placement and placing a stent in the parent artery requires prolonged use of anti-platelet agents to reduce the risk of thrombosis-based stenosis within the stent.

Some aneurysms and fistulas are ideally treated with covered stents, which can most directly cover the hole of the fistula or the neck of the aneurysm and reconstruct the vessel wall, immediately redirecting blood flow into the normal path of the parent vessel. However, there is no covered neuro-stent currently available in the United States. The U.S. Food and Drug Administration (FDA) has examined and tested such covered neuro-stents but none has "FDA approval," which means that the FDA has not decided the benefits of the previous versions of covered neuro-stents outweigh the potential risks for the item's planned use. Additionally, there are currently no covered stents that are effective in severely tortuous anatomy in other parts of the body, including but not limited to splenic artery aneurysms and pulmonary arteriovenous fistulas.

A potentially significant use of covered neuro-stents is for the treatment of fistulas, particularly for Carotid cavernous fistula (CCF) which is an abnormal communication between the cavernous sinus and the carotid arterial system.

Other treatment of aneurysms includes surgical clipping of an intracranial aneurysm, which involves the application of a clip across the neck of the aneurysm. This treatment has several shortcomings including that it requires an open operation and physical manipulation of the brain. Sometimes surgical bypass is considered as well, but typically is associated with even higher rates of morbidity and mortality.

Additionally, prior art teaches the use of flow diversion devices to divert flow away from the aneurysm by placing a mesh stent or a structure similar to a stent, on the aneurysm neck along the parent artery. The use of these devices allows for thrombus formation inside the aneurysm. However, increased technical complications can develop following the deployment of flow diverters. Additionally, because they do not completely block flow, they are not effective in the treatment of fistulas and ruptured vessel. Similarly, there is currently no effective vessel-sparing treatment of an iatrogenic rupture of an intracranial artery. Current treatment requires closing the ruptured artery with coils and/or liquid embolics to stop the bleeding, usually with significant resulting morbidity from ischemic injury to that arterial territory. Furthermore, when treating aneurysms with these devices, the aneurysm thromboses over time, a lag period, and is not immediately cured. This leaves the patient at risk of aneurysmal rupture during lag period. This can be especially problematic when treating ruptured aneurysms, which have high short-term re-rupture rates.

A need exists for an endovascular device capable of endovascular intervention for immediate cure of select intravascular aneurysm or fistula, while ameliorating the difficulties and shortcomings associated with the currently available technologies. More particularly, a need exists for a covered stent which allow said stent freedom of motion and bending without kinking around tight bends in tortuous anatomy.

Most covered stents involve producing a cylinder of a stent "skeleton" or "frame" out of semirigid materials such as metal alloys, and then attaching an impermeable "cover" to said frame. The prior art teaches such attachments are diffuse and located throughout the covering of a stent, along fixed intervals of said covering and frame, and consequently significantly limit flexibility of the device. The present invention teaches a covered stent device capable of safe and effective delivery and deployment into tortuous vessels to effectively diverting blood flow away from an aneurysm, fistula, or ruptured vessel while allowing blood to flow to healthy tissue distal to the targeted treatment area and still resulting in blood stasis and thrombus formation inside the aneurysm or fistula. Thus, a need exists for a covered neuro stent as well as a covered stent which is capable of use in other tortuous anatomy outside of brain. The present invention satisfies this need.

SUMMARY OF THE INVENTION

The present invention is a stent with a free-floating cover. Said floating cover is designed to optimize insertion in tortuous anatomy. Among its unique structural elements are a single circumferential attachment point at one end (as small as 1 nm), overlapping circumferential shingles and overlapping geometric shingles.

In one embodiment, said geometric shingles are triangles attached on one end. Said shingles would overlap like scales on a fish.

Such single circumferential or longitudinal attachment point optionally combined with said overlapping circumferential shingles allow the present invention to bend without kinking. This feature will allow sufficient flexibility to warrant its use as a covered neuro stent as well as to be useful in other tortuous anatomy outside of brain as well.

In other embodiments, said overlapping geometric shingles may have attachment to said frame on only one side, comprising less than 70% of the length of said shingles, with said shingle optionally being attached only along a limited segment of the circumference or longitudinal surface of said frame, with additional overlapping shingles and their independent attachments extending over a covered segment or segments of the stent, thus resulting in complete coverage of said segment(s) of the stent.

The disclosed device may optionally be deployed under flow arrest, via pharmacologic means, or via delivery through a balloon guide catheter with temporary balloon inflation or other means, to minimize the possibility of blood flow folding or bunching the fabric as it is unsheathed.

In still other embodiments, said coverings may not fully encircle a given segment of said frame, thus allowing some stents to be covered along a portion of its circumference while being uncovered at a different circumferential side of the same segment. This can sometimes allow preservation of the origin of a branch vessel that might arise from the parent vessel along the same segment of said parent vessel; for example, opposite to a fistula or the neck of an aneurysm.

DETAILED DESCRIPTION OF THE INVENTION

Figure 1:
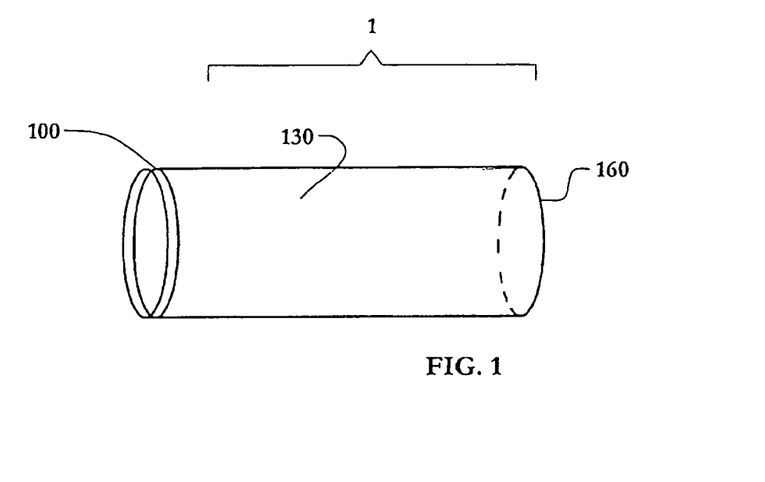
FIG. 1 shows the cape element 1 of the present invention, having an impermeable seal element 130, cape attachment element 100, and a free end 160.
Figure 2:
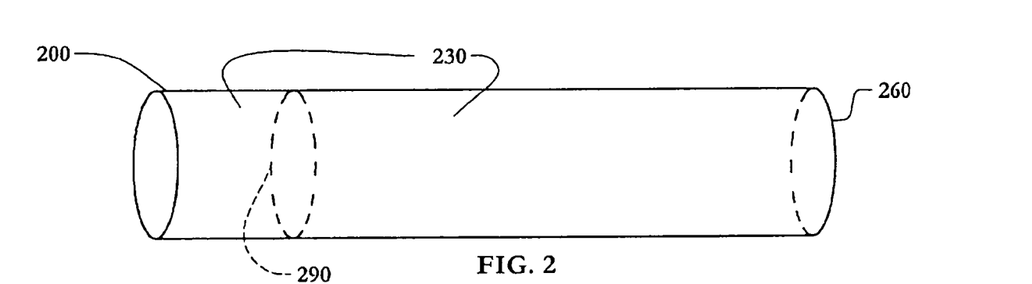
FIG. 2 depicts a translucent, permeable stent 230 element, having a first end 200, a second end 260, and stent attachment element 290; the permeable mesh is not shown (to highlight attachment element 290).
Figure 3:
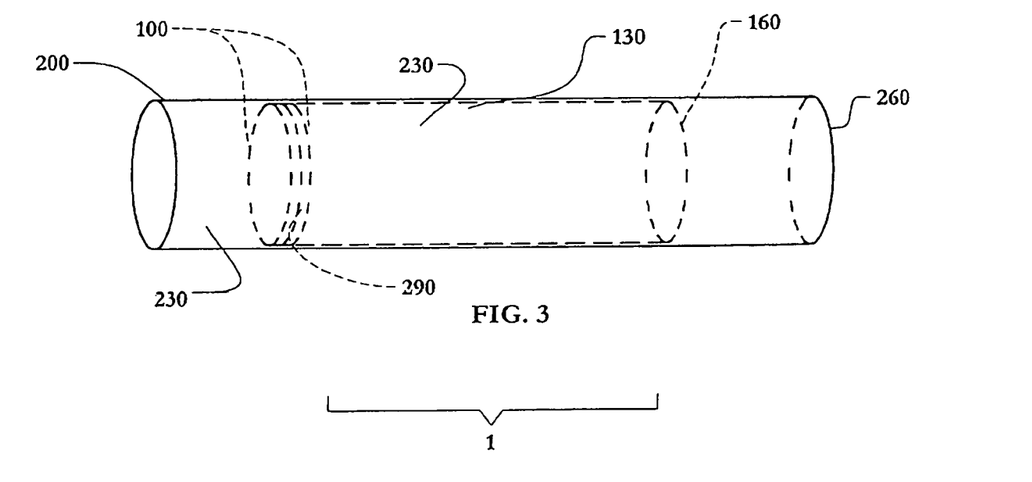
FIG. 3 shows the cape element 1 of FIG. 1 attached where stent element 290 meets cape element 100.
Figure 4:
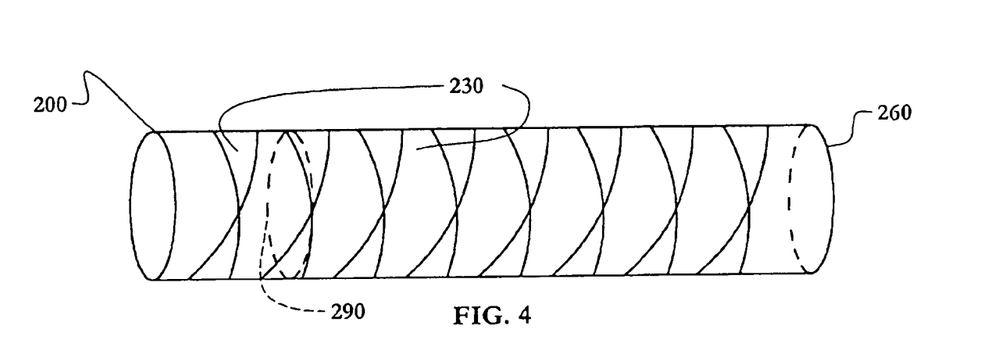
FIG. 4 shows the stent element 230 of FIG. 2, substituting wire struts for a stent mesh with small permeable openings.
Figure 5:
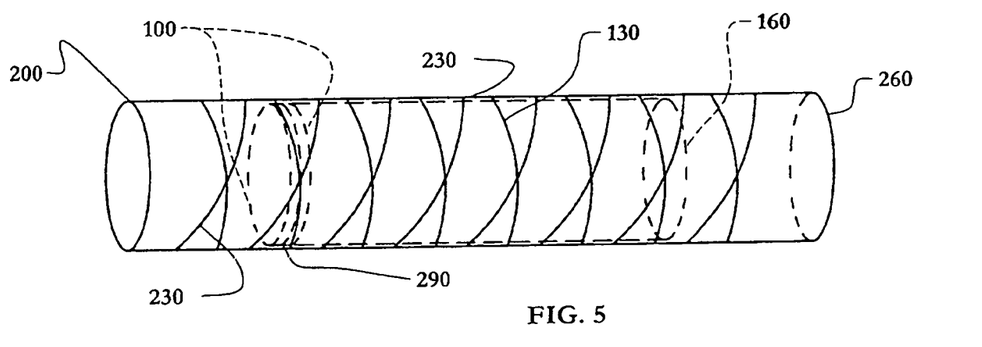
FIG. 5 shows the same elements as FIG. 3, substituting wire struts for a stent mesh with small permeable openings.

Referring now to FIGS. 1-3, in a preferred embodiment, seal element 130 is attached to a stent body 230 by connection element 100 on cape element 1 to attachment element 295 on stent 230. Seal element 130 varies in length (from connector 100 to free end 160) according to the size of the target vessel. The seal 130 should be approximately 30% longer than the area of the target vessel intended to be covered in order to prevent rigidity at bends. More particularly, insofar as the cover 130 is only attached to stent 230 outside the seal-deployment area, the stent 230 will be more flexible than a stent having a cover attached throughout.

An advantage of the current invention is that stent 230 is allowed to move at sharper angles than covered stents of the prior art. This feature means that the current invention presents no sharp edges which can lead to abrasion, puncture, rupture or other damage to the target vessel while allowing better conformance to the vessel wall in addition to a continuous seal. The cape design of the current invention eliminates, or at least ameliorates, rigidity associated with covered stents by allowing free movement of the cape-cover 1. This feature allows the user easier deployment of the current invention than existing covered stents because the prior art forces the covering to distend when bent, thus increasing stiffness.

In an alternate embodiment the cylinder of fabric is on the outside of the skeleton of stent 230. The preferred embodiment has this configuration, with the attachment on the distal end (spanning a punctate/very short distance) of the covered zone. The covering can cover anywhere from 1% to 100% of the stent. In the preferred embodiment it covers the central or medial portion of the stent 230 skeleton while leaving the first end 200 and second end 260 of the skeleton uncovered. In the preferred version the attachment zone is circumferentially around the stent in a distal position, making delivery easier. However, it can be proximal as well. This design results in covered stents which can more freely bend along the contour of tortuous vessels, without kinking or straightening the vessel, compared to prior stents that had multiple or diffuse attachments between the "fabric" and the skeleton. The outer end of any curve requires a larger radius than the inner curve and the diffuse attachments of a typical covered stent require a fixed amount of fabric per interstices or zone of the stent, thus making the more usual configuration much more stiff.

The device of the present invention is deployed using a microcatheter or sheath (not shown). It may be deployed either out an end hole or side hole thereon. The present invention may be deployed via a balloon or wire.

The present invention may attach cape 1 to stent 230 either toward the distal end of stent 230 or the proximal end of stent 230. When stent 230 is deployed using a balloon (not shown) to activate the present invention, then the preferred embodiment is to attach cape 1 toward the proximal end of stent 230 because the balloon pushes the present invention open. When stent 230 is deployed using a wire (not shown) to activate the present invention, then the preferred embodiment is to attach cape 1 toward the distal end of stent 230 because the wire pulls.

In one embodiment of the present invention a separate stent 230 skeleton with an attached inner cylinder of covering "fabric" such as nylon, Dacron, pericardium, polyester, PET, PTFE or any other nonporous or minimally porous material, wherein the inner cylinder of fabric is only attached on one side, such as the distal end of the fabric or the proximal end of the fabric, to the skeleton. The attachment zone can be from as small as a punctate point circumferentially around the stent, to as much as 70%. In the preferred version the attachment point 135 would be very short. In the preferred version the "fabric" layer is outside the "frame/skeleton" layer. Alternatively, the "fabric" layer can be on the inside.

Figure 6:
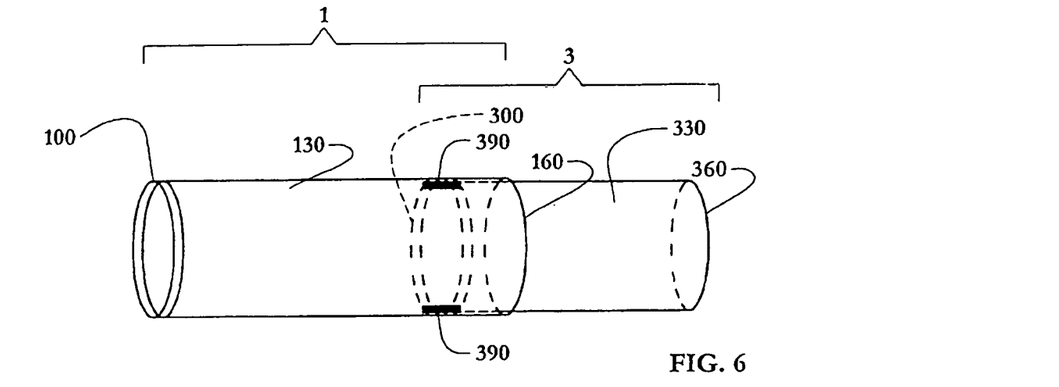
FIG. 6 shows how a first caped element 1 and a second caped element 3 are joined where telescope attachment element 390 located on cape element 1 between cape attachment element 100 and free end 160 meets attachment element 300 located on cape element 3.
Figure 7:
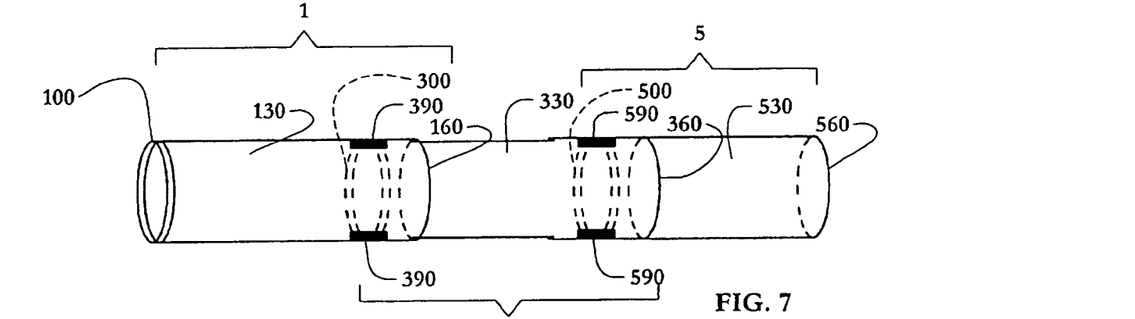
FIG. 7 shows how three caped elements are coupled. In particular, a first cape element 1, a second caped element 3 and a third cape element 5 are joined. Cape elements 1 and 3 are joined as described in FIG. 6 above. Second caped element 3 and a third cape element 5 are joined where telescope attachment element 590 located on cape element 3 in between cape attachment element 300 and free end 360, and meets telescope attachment element 500 located on cape element 5.
Figure 8:
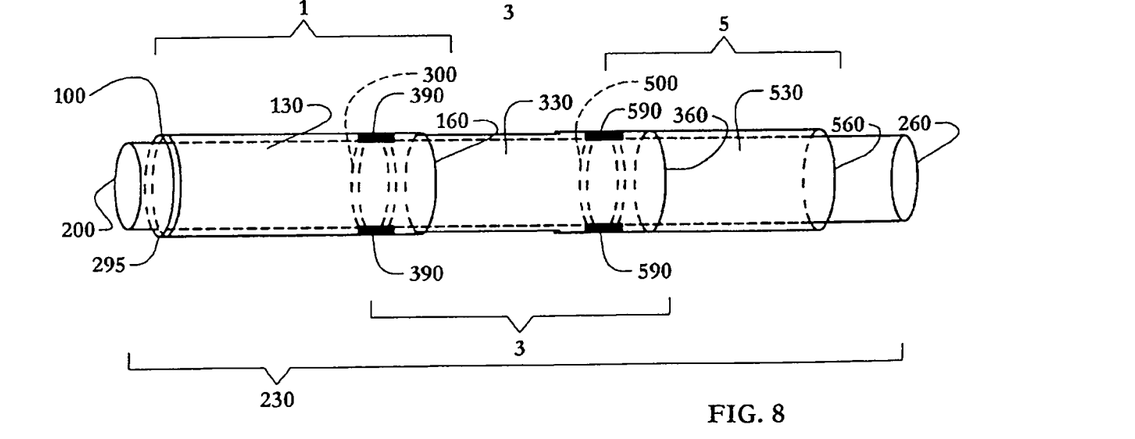
FIG. 8 shows all the elements of FIG. 7 with stent 230 passing through it. All caped elements are attached to stent 230 at a single point attachment 295. Additionally, element 100 of first caped element 1 fixes first cape element 2 to the stent at attachment element 295, located on stent 230 between first end 200 and second end 260.
Figure 9:
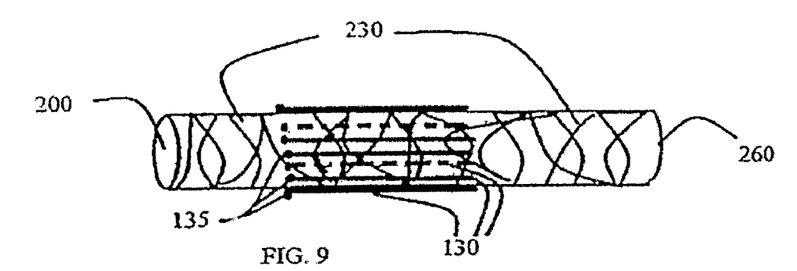
FIG. 9 is a side view of an alternate embodiment of a set of undeployed seal elements 130 joined at linear connection points 135 on the outer surface of stent 230 in the linear axis.
Figure 10:
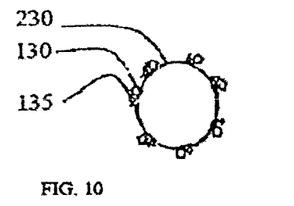
FIG. 10 is a top view from first end 200 of the undeployed stent 230 of FIG. 9, showing coiled seal elements 130 adjacent to connection points 135 attached to stent 230 disposed on the outer surface in the linear axis.
Figure 11:
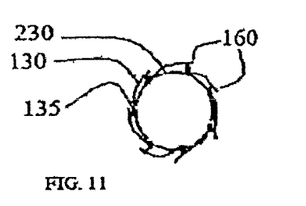
FIG. 11 depicts stent 230 of FIG. 10 in a deployed state, showing a plurality of unrolled seal elements 130 with each free end 160 making a flap over the first end 100 at the adjacent linear connection points 135 to form a fanfold-type overlap covering stent 230.
Figure 12:
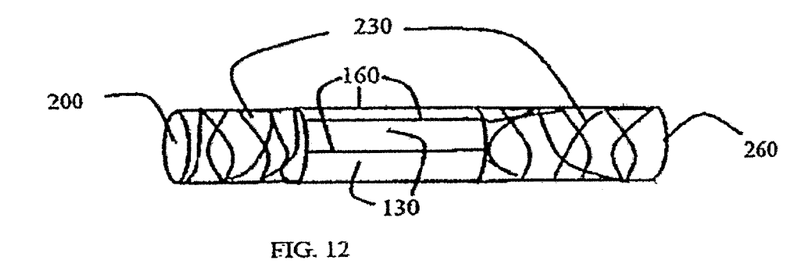
FIG. 12 is a side view of the embodiment of FIG. 9 in a deployed state, showing unrolled seal elements 130 forming a coverage band of overlapping free ends 160 about the medial circumference of stent 230.

Referring now to FIGS. 6-8 disclosing the overlap in between coverings, cover 1 overlaps 3, and 3 overlaps 5 by way of illustration to create an impermeable shingling effect. Said shingling effect is a significant improvement over prior art covered stents because each cape (1, 2 or 3) may be deployed completely without fully deploying other capes. The advantage is that a fistula may be covered without fully deploying the entire covered stent. Another advantage of this feature is that the present invention ameliorates the need for different-sized covered stents.

Figure 13:
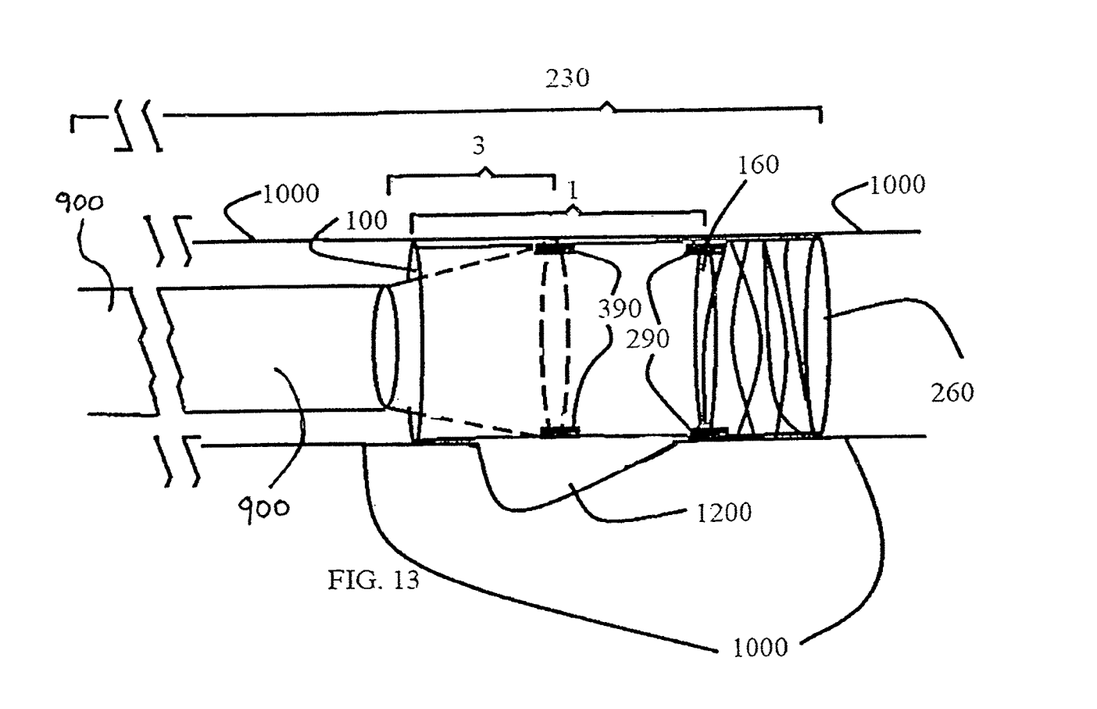
FIG. 13 is a side view of a self-expanding stent body in the process of deployment by delivery device 900 within target vessel 1000, wherein cape 1 is fully deployed, illustrating that fistula 1200 is covered prior to full deployment of cape 3.

Now referring to FIG. 13, which depicts the present invention covering a fistula without being fully deployed.

Referring now to FIGS. 9-12, in alternative embodiments the covered stents 230 instead of having a single continuous sheet there are multiple circumferentially 'shingled' sheets 1 of fabric, wherein the nonattached or free segment 160 of sealing fabric 130 from one sheet overlaps with the attached segment of the next sheet. This shingling allows the stent to more freely bend in zones where there is no attachment. The shingles can be on the inner surface or outer surface of the stent 230 skeleton or scaffold.

In yet another embodiment of the present invention the "fabric" is circumferential inside (not shown) or outside the skeleton, and has multiple intermittent circumferential attachment points 135 to the skeleton 230, but has excess length of "fabric" at free end 160 compared to "frame/skeleton" at the optimal diameter in each segment between the attachments, to allow the skeleton to bend freely without being restricted by the fabric (the extra fabric will allow relative lengthening of the skeleton on the outer side of bends in the anatomy).

In a final embodiment of the present invention a similar shingling is used as in the foregoing embodiment, but the shingled capes 1, 2 or 3 comprise various geometric shapes that are not necessarily circumferential around the entire stent. Nonlimiting examples multiple triangles, wherein the covered segment has shingling that will effectively entirely cover the "covered" zone. Again, the shingled coverings can be disposed upon the inner surface or outer surface of the skeleton.

All embodiments can optionally have at least one uncovered opening in the covered.

All embodiments can optionally have multiple covered zones.

All embodiments can optionally have multiple uncovered zones.

Optional in all embodiments of the present invention may be a second telescoping stent, either on the inside for versions that have the "fabric" on the inside or on the outside for versions that have the fabric on the exterior of the skeleton, that can be used to pin the fabric between the two layers of skeleton. The second telescoping stent can either be a second built-in layer with the fabric layer sandwiched in between (but the fabric mostly unattached), or in the preferred embodiment of this optional additional stent layer it is placed separately as a separate, non-attached layer/device. This second skeleton can often minimize the risk of endoleaks at the non-attached regions. Endoleaks can be minimized where the "fabric" layer is not fully attached, if a second stent does not pin the "fabric" to the first then some of the fabric layers may have some freedom of movement—especially in regions where they are covering and aneurysm or a fistulous hole and not pinned fully to a vessel wall- and when they have some freedom of motion after implanted, blood flow can potentially sometimes flap them open, especially in the "shingled" version.

The present invention optionally includes an additional structure to minimize endoleaks. In particular each embodiment may have optional adhered hydrogel.

The "skeletons" of all embodiments of the present invention are composed of semi-rigid but flexible materials, such as metal alloys (containing chromium cobalt, and/or platinum, and/or nickel, titanium, steel, etc.) or synthetic fibers such as vicryl.

All elements of the present invention may be biodegradable or nondegradable. Alternatively, the present invention may be composed of both biodegradable or nondegradable elements. Element being complete components of a particular part of the present invention or sub-components of each part.

The present invention may employ self-expanding components.

The present invention may employ balloon-expanding components.

The present invention may optionally contain radiopaque components and/or radiopaque markers. These can be especially valuable at ends of stent and at the ends of covered zone. Radio-opaque materials and markers can also be optionally present in more places, and sometimes throughout.

The present invention's overlapping, underlapping, and/or shingled "fabric" layers may optionally have an additional "frame/skeleton" lattice supporting it, wherein that skeleton/frame is primarily supporting that "fabric" layer, and is an independent (but attached) skeleton layer to the main skeleton cylinder of the stent. For example, if there are triangular shingles of "fabric" attached on one end of the triangles to the outside of a metal skeleton/cylinder, each triangle of "fabric" may optionally have additional metal struts supporting it, provided such a skeleton is primarily free from the main cylinder (i.e.—no more than 70% of the support skeleton for unattached portion of the "fabric" is attached to the main skeleton stent/cylinder).

The present invention may have branched stent elements.

The present invention's stent elements may optionally be fully re-sheathable.

The present invention's stent elements may optionally be partly re-sheathable

All stent elements of the present invention may be optionally be detachable.

It should be noted that one representative example of a "Skeleton" and "fabric" layer, before their attachment (attachment in manufacturing process) attachment length (relative to "fabric") can be as small as 0.00001% and as much as 70%.

In this embodiment, the fabric is preferably attached at a distally punctate location such that it covers a percentage of the skeletal surface. In a preferred embodiment the fabric is attached upon the outside of the skeleton such that it will contact the vascular walls upon deployment. The fabric uncoils together with the skeleton upon deployment. In an alternate embodiment, the fabric is attached on the interior surface such that it is disposed within the stent skeleton. In this configuration, the skeletal surface abuts the vessel wall.

The degree of overlap varies depending upon the diameter of the expanded stent skeleton and the lumen within which it is deployed. For example, in a 2 mm vessel, a 6 mm stent has an overlap of approximately two-thirds, whereas a 4 mm stent overlaps about two-fifths; in a 4 mm vessel the 6 mm stent overlaps about a third, and the 4 mm stent only about $2/25$ths (8%).

For clarity, the overlap of a coil-type stent skeleton is different from the optional embodiment of overlapping fabric capes (or covers) as described hereinabove. Overlapping stents overlap longitudinally, in the manner of fanfold or unrolled map. Overlapping capes or covers overlap in a telescoping manner.

In still another embodiment (not shown) the stent skeleton is a semi-cylindrical, having a discontinuous diameter and longitudinal edges overlapping in a loose coil in an undeployed state. The stent unrolls into an overlapping but substantially cylindrical shape as the skeleton expands when inserted in a target vessel. In such stent configurations, the cape of the current invention will be attached longitudinally.

It will be understood by those skilled in the art that the above particular embodiments are shown and described by way of illustration only. The principles and the features of the present disclosure may be employed in various and numerous embodiments thereof without departing from the scope and spirit of the disclosure as claimed. The above-described embodiments illustrate the scope of the disclosure but do not restrict the scope of the disclosure.

What is claimed is:

1. An intravascular stent comprising:
   (a) a stent body and at least two stent capes dimensioned to cover a portion of the stent body, the at least two stent capes extending parallel to said stent body; wherein said at least two stent capes are impermeable;
   (b) each of said at least two stent capes having a first end and a second end, wherein said first end and second end are parallel to a longitudinal axis of said stent body, a first stent cape of the at least two stent capes is attached to said stent body along an attachment segment;
   (c) wherein said attachment segment is attached to an external surface of said stent body;
   (d) said second end adapted to move freely about said stent body;
   (e) wherein said at least two stent capes expand independently of said stent body and independent of each other upon deployment of said stent body;
   (f) said at least two stent capes are oriented circumferentially upon said stent body, wherein each of said at least two stent capes extend partially about a circumference of the stent body to cover less than a full circumference of the stent body and a second stent cape of the at least two stent capes overlaps the first stent cape of the at least two stent capes.

2. The at least two stent capes according to claim 1, wherein said at least two stent capes partially circumferentially cover said stent body such that blood may flow to a branch in a target vessel.

3. The intravascular stent according to claim 1, wherein said second end of one of said at least two stent capes overlaps the first end of another of said at least two stent capes in a shingling arrangement.

4. The intravascular stent according to claim 1, wherein the second end of a first stent cape of the at least two stent capes overlaps the attachment segment of a second stent cape of the at least two stent capes and covers only a portion of the second cape stent.

5. The intravascular stent according to claim 1, wherein the at least two stent capes are inserted in a rolled configuration and when deployed move to an unrolled configuration.

6. An intravascular stent comprising:
   (a) a stent body and at least a first stent cape and a second stent cape, the first and second stent capes dimensioned to cover a portion of the stent body, wherein the first and second stent capes are impermeable and overlap;
   (b) each of the stent capes has a first end and a second end, wherein the first end has an attachment segment for attachment to the stent body and the second end is a free end unattached to the stent body and adapted to move freely with respect to the stent body;
   (c) wherein the first and second stent capes expand independently of said stent body and independent of each other upon deployment of said stent body.

7. The intravascular stent of claim 6, wherein the first stent cape extends radially about a first circumferential region of the stent body and the second stent cape extends radially about a second circumferential region of the stent body, and a region of the first stent cape overlaps a region of the second stent cape, wherein the first and second circumferential regions extend about a circumferential arc which extends less than 360 degrees.

8. The intravascular stent according to claim 6, wherein the first and second stent capes form outer layers of the stent and the attachment segments of the first and second stent capes are contiguous with the stent body.

9. The intravascular stent according to claim 6, wherein the second end of the first stent cape overlaps the first end of the second stent cape and does not overlap the second end of the second stent cape to form a shingle configuration.

10. The intravascular stent according to claim 6, wherein the second end of the first stent cape overlaps the attachment segment of the second stent cape.

11. The intravascular stent according to claim 6, wherein the stent is inserted into the vessel with the first and second stent capes attached to the stent body in a shingle arrangement.

12. The intravascular stent according to claim 6, wherein the first and second stent capes form outer layers covering only a portion of the stent body.

13. The intravascular stent according to claim 6, wherein a majority of the first stent cape and a majority of the second stent cape are free floating.

14. The intravascular stent according to claim 6, wherein the first and second stent capes are inserted in a rolled configuration and when deployed move to an unrolled configuration.

15. An intravascular stent comprising:
   (a) a stent body and at least a first stent cape and a second stent cape, the first and second stent capes dimensioned to cover a portion of the stent body, wherein the first and second stent capes are impermeable and overlap;

(b) each of the stent capes has a first end and a second end, wherein the first end has an attachment segment for attachment to the stent body and the second end is a free end unattached to the stent body and adapted to move freely with respect to the stent body;

(c) wherein the first and second stent capes are attached to the stent body prior to being inserted and placed within the vessel.

16. The intravascular stent according to claim 15, wherein the first stent cape and the second stent cape are oriented circumferentially upon said stent body, wherein each of said first and second stent capes extend partially about the circumference of the stent body to cover less than a full circumference.

17. The intravascular stent according to claim 15, wherein the first and second stent capes only partially overlap.

18. The intravascular stent according to claim 15, wherein the second stent cape overlaps the attachment segment of the first stent cape.

19. The intravascular stent according to claim 15, wherein the at least two stent capes are in a rolled configuration when the stent is inserted and move to an unrolled configuration after insertion and expansion of the stent.

20. The intravascular stent according to claim 15, wherein a majority of the first stent cape and a majority of the second stent cape are free floating.

* * * * *